United States Patent
Lin et al.

(10) Patent No.: US 8,045,685 B2
(45) Date of Patent: Oct. 25, 2011

(54) MOVABLE MONITORING EQUIPMENT AND REMOTE MONITORING AND DIRECTING SYSTEM

(75) Inventors: John Lin, Hsinchu County (TW); Kuo-Hung Chan, Hsinchu County (TW); Wen-Chen Chang, Hsinchu (TW); Shih-Yang Kou, Hsinchu (TW); Tzeng-Yow Lin, Tainan (TW); Wai-Mau Choi, Taipei (TW); Hsueh-Hai Hu, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 1334 days.

(21) Appl. No.: 11/617,745

(22) Filed: Dec. 29, 2006

(65) Prior Publication Data
US 2008/0046911 A1     Feb. 21, 2008

(30) Foreign Application Priority Data
Jul. 19, 2006     (TW) .............................. 95126336 A

(51) Int. Cl.
H04M 11/00     (2006.01)
(52) U.S. Cl. ..................................... 379/106.02; 379/38
(58) Field of Classification Search ............. 379/106.02, 379/38; 348/14.01, 14.08, 14.09
See application file for complete search history.

(56) References Cited

U.S. PATENT DOCUMENTS

| | | |
|---|---|---|
| 6,416,471 B1 | 7/2002 | Kumar et al. |
| 2002/0191744 A1 | 12/2002 | Mirabella |
| 2004/0179092 A1 | 9/2004 | LaPoint |
| 2007/0299473 A1* | 12/2007 | Matos ............................... 607/5 |

* cited by examiner

Primary Examiner — Stella Woo
(74) Attorney, Agent, or Firm — Jianq Chyun IP Office

(57) ABSTRACT

A remote monitoring and directing system including at least one video camera at the first-aid side to observe the situation of casualty and the operation on the casualty is provided. At least one microphone is disposed at the first-aid side for communicating with the first-aid personnel and directing a clinical operation. At least one medical instrument standard interface is disposed at the first-aid side for transmitting the electrocardiogram or other physiological information. At least one video/audio and data server is disposed at the monitoring side for managing information integration. A plurality of authorized computer systems is set up for conferring with and directing the first-aid station or the ambulance via the Internet, so as to give a direction. A wireless or cable connection is used for the conference between the first-aid side and the monitoring side.

11 Claims, 3 Drawing Sheets

MOVABLE MONITORING EQUIPMENT AND REMOTE MONITORING AND DIRECTING SYSTEM

CROSS-REFERENCE TO RELATED APPLICATION

This application claims the priority benefit of Taiwan application serial no. 95126336, filed Jul. 19, 2006. All disclosure of the Taiwan application is incorporated herein by reference.

BACKGROUND OF THE INVENTION

1. Field of the Invention

The present invention relates to an event monitoring technology. More particularly, the present invention relates to an integrated monitoring equipment and system which can be used for, for example, first-aid monitoring and directing.

2. Description of Related Art

Normally medical resources at remote area are very limited, and it may take up to a few hours to send a casualty of serious illness to the hospital by an ambulance. During such primary rescue period, if the daily first-aid trainings of first-aid personnel and some of the medical instruments can be utilized well, and with the instant on-line medical instructions of doctors in the hospital, the survivability of the casualty can be increased greatly.

The provision of accurate information of the casualty may also prevent such situation that the casualty has to be transferred to another hospital after he/she is sent to the hospital. In addition, the ambulance can be dispatched to the spot instantly through the provision of the geographical information of the ambulance. Moreover, the hospital can finish its preparations in various aspects before the casualty reaches the hospital, so that the first-aid time can be under control.

Furthermore, when major disaster or accident happens, the first-hand in situ videos provided to the hospital, the emergency first-aid unit, or even the government decision-making unit can help the foregoing units to deal with the emergency situation by dispatching appropriate number of ambulances to the spot.

As described above, in conventional technology, such as the U.S. Patent Publication No. 2002/0191744, the information of the casualty can be obtained in advance. FIG. 1 is a diagram of a conventional first-aid system. Referring to FIG. 1, when the ambulance 100 carries a casualty 102 to an appointed hospital, the casualty 102 can be examined with the instrument 104 in the ambulance 100, and the information obtained is sent out as wireless signal 108 through a wireless transmission system 106. In the hospital, the electrocardiogram can be displayed on a display 114 through the receiving unit 110 and the signal processing unit 112 to be looked at by the medical worker 116.

Basically, conventional first-aid manner has following disadvantages.

The system has to be carried by a large-sized vehicle instead of being installed on a regular ambulance, so that it is not suitable for rough and cross-country road. Besides, the portability of the system is not good and which makes it difficult to move the system out of the vehicle.

The conventional system is an one-to-one system which can not perform multiple-to-multiple information transmission.

In the conventional system, the exact location of the vehicle and the accurate arrival time cannot be obtained, and management of multiple ambulances cannot be achieved.

The conventional system cannot instantly transmit video/audio, give medical first-aid instruction, or give online advice (for example, heart electroshock).

Accordingly, improved processing methods to the foregoing disadvantages in conventional first-aid manner are provided in the present invention, and which will be described below.

SUMMARY OF THE INVENTION

Accordingly, the present invention is directed to provide a movable monitoring equipment which can be disposed somewhere freely and movably according to requirement for instantly transmitting signals generated by instruments and videos, location of an accident spot.

According to the present invention, the movable monitoring equipment can also provide instant process to remote event besides first aid to casualty.

The present invention provides a remote monitoring and directing system, which can achieve the instant integration between local and remote sides, or even between first-aid sides by using monitoring equipment, so as to accomplish instant process when an event occurs.

The present invention provides a movable monitoring equipment which includes a video capturing unit for capturing a video signal, an audio unit for producing and receiving an audio communication signal so as to communicate with a remote system, an instrument interface unit for transmitting a medical instrument examination signal, and a signal processing unit coupled to the video capturing unit, the audio unit, and the instrument interface unit for processing the outputs and inputs of the foregoing units respectively, so as to output at least one signal string and transmit information back and forth with a remote side through a network.

The present invention further provides a remote monitoring system for providing emergent process on the spot of an event by using the equipment described above.

The present invention provides a remote monitoring and directing system which is set up at the occurrence of an event. The system includes a spot-side subsystem and a monitoring-side subsystem and information is bi-directionally communicated through a network. The spot-side subsystem includes at least one video capturing unit for capturing a video signal, at least one audio unit for producing and receiving an audio communication signal so as to communicate with the monitoring-side subsystem, at least one instrument interface unit for transmitting at least one instrument examination signal, and a signal processing unit coupled to the video capturing unit, the audio unit, and the instrument interface unit for processing the outputs and inputs of the foregoing units respectively, so as to output at least one signal string. The spot-side subsystem is coupled to the monitoring-side subsystem through the network.

The monitoring-side subsystem can be directed and controlled by at least one director. The monitoring-side subsystem includes at least one information transceiver interface for receiving the signal string or sending a response signal; at least one signal processing unit for processing the signal string so as to obtain at least one information content carried by the signal string; and at least one video/audio unit for receiving a video/audio content of the information content to display and communicate.

In order to make the aforementioned and other objects, features and advantages of the present invention comprehensible, a preferred embodiment accompanied with figures is described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

The present invention is applicable to first aid, wherein a remote authorized party can observe, discuss, and give online medical instruction by transmission of on-site instant video/audio and physiological information. Also and, the clinical operation performed by a first-aid worker and changes of the physiological information of the casualty can be observed instantly by the authorized party, thus, the purpose of remote first aid and medical treatment can be achieved. The present invention can be applied to such situations as ambulance emergency first aid, setting up emergency first-aid station, inter-hospital transfer, coordinating between emergency first-aid units, online medical conference, and online medical advices. According to the present invention, the medical directions of doctors can be fully extended, the primary treatment time can be well controlled, and the standard of medical emergency response and treatment can be improved considerably, thus, the present invention has very large commercial potential.

Moreover, the present invention can also be applied to the instant processing of a remote event. The video of the spot and the data examined with instruments can be transmitted instantly, so that the monitoring side can direct the on-site personnel to perform appropriate process. In addition, if necessary, an engineering truck can be sent by rescue unit. The location of the engineering truck can also be obtained instantly, which is advantageous in prearranged processing.

Some embodiments of the present invention are described below; however, the present invention is not limited thereto.

Figure 1:
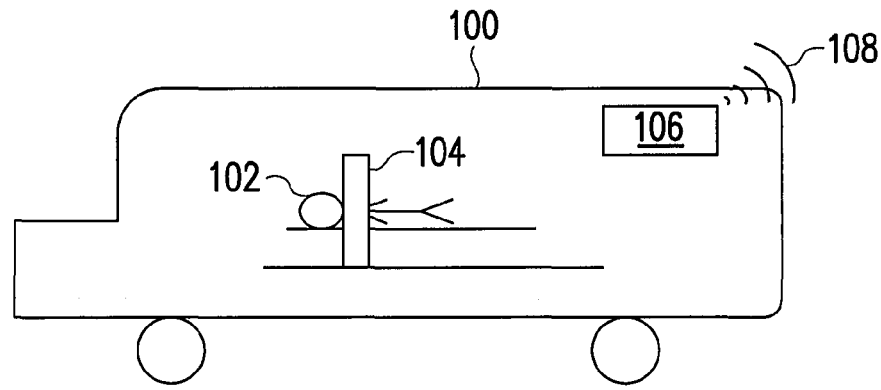
FIG. 1 is a diagram of a conventional first-aid system.
Figure 1:
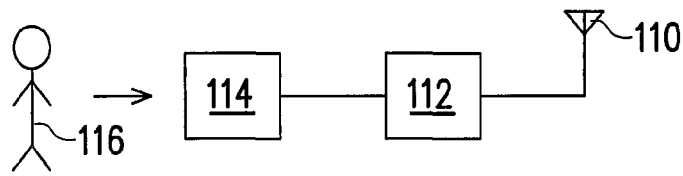
Figure 2:
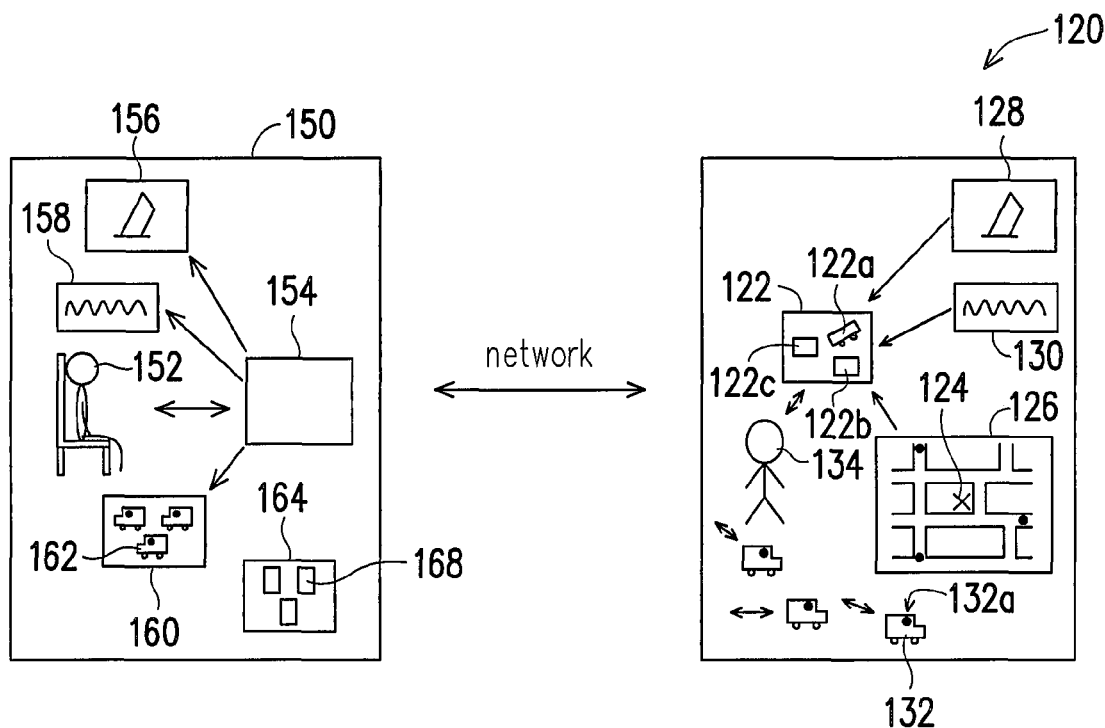
FIG. 2 is a diagram of a remote monitoring and directing system according to the present invention.

FIG. 2 is a diagram of a remote monitoring and directing system according to the present invention. Referring to FIG. 2, on the spot of an event or a remote first-aid side, a spot-side subsystem 120 is set up. The spot is, for example, the accident spot of a collapsed building. The spot-side subsystem 120 is disposed with a movable monitoring equipment 122. In other words, at the beginning of the event, the monitoring staff dispatches someone to dispose the movable monitoring equipment 122 at a desired place properly, so as to set up a system for monitoring and directing. It is the content and operations after the system has been set up described in the embodiments of the present invention.

Figure 3:
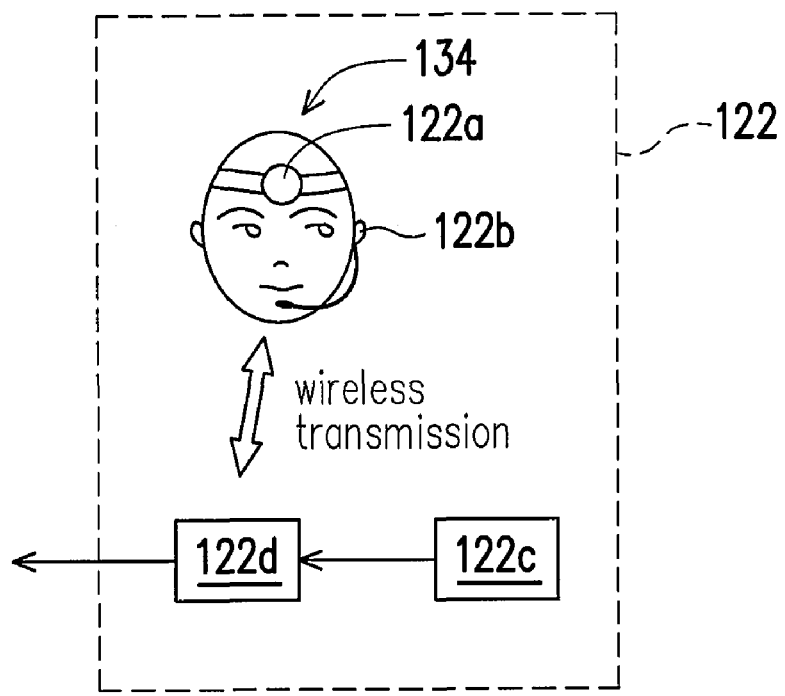
FIG. 3 is a diagram illustrating the implementation of a monitoring equipment 122 according to an embodiment of the present invention.

The movable monitoring equipment 122 includes: a video capturing unit 122a for capturing a desired video signal, which may be, for example, an accident scene 128. Further, an audio unit 122b is used for producing and receiving an audio communication signal, so as to communicate with the remote system, An instrument interface unit 122c is used for transmitting at least one instrument examination signal produced by an examination instrument 130, such as an electrocardiogram, other physiological information, or some physical signals measured on the spot. A signal processing unit 122d (as shown in FIG. 3) is coupled to the video capturing unit 122a, the audio unit 122b, and the instrument interface unit 122c for processing the outputs and inputs of the foregoing units respectively, so as to output at least one signal string and transmit information back and forth with a remote side through a network.

The video capturing unit 122a, the audio unit 122b, the instrument interface unit 122c, and the signal processing unit 122d are combined into a movable entity. The method of transmitting information with the remote side is, for example, through wireless network or cable network. The wireless method may be, for example, Bluetooth, infrared ray, WCDMA, satellite communication, . . . etc. Besides, the coupling between the video capturing unit 122a, the audio unit 122b, and the instrument interface unit 122c and the signal processing unit 122d may also be cable or wireless which allows the on-site worker 134 to walk around and obtain the desired information. In addition, a positioning system 126 coupled to the signal processing unit 122d (as shown in FIG. 3) is disposed on the movable monitoring equipment 122, which can provide the location, for example, the location of the accident spot 124, by displaying an electronic map through the global positioning system (GPS). The location of the accident spot 124 can also be transmitted to the monitoring-side subsystem 150 through the signal processing unit 122d. The application of the movable monitoring equipment 122 will be described below.

The spot-side subsystem 120 also cooperates with a first-aid subsystem and a monitoring-side subsystem 150 along with the cooperation of the entire system. The first-aid-side subsystem includes a first-aid unit. The first-aid unit includes, for example, at least a first-aid group 160 and a medical group 164. In the embodiment of FIG. 2, the first-aid unit is set up by, for example, the director 152 of the monitoring-side subsystem 150 according to the actual requirement. Certainly, the first-aid unit may also be set up permanently and receive the dispatch and instruction of the director 152 at any time. The setting-up of the first-aid unit can be arranged differently as long as the first-aid unit can accomplish instant first-aid purpose, and FIG. 2 is only an embodiment. The first-aid group 160 includes, for example, at least an ambulance/first-aid station 132, 162, and the medical group 164 includes, for example, at least one hospital 168. In addition, the ambulance/first-aid station 132, 162 and the medical group 164 are under dispatch or direction of the director 152 in the monitoring-side subsystem 150 or other related personnel, and the details thereof will not be described herein. It should be noted that the ambulance/first-aid station 132, 162 are also disposed with the foregoing movable monitoring equipment 122, so as to obtain the actual situation and emergency first-aid process of the casualty instantly. The GPS 132a can provide the location of the casualty, for example, the location (denoted with a dot) on the electronic map in the positioning system 126. Accordingly, the number and movements of the ambulances can be under control at any time. The target hospital or the on-site work 134 can estimate the arrival time and prepare in advance, so as to improve processing efficiency. There are some examination instruments 130 at the accident spot 124 and the ambulance/first-aid station 132, 162 for physiological or physical examinations. All the information can be sent out.

The monitoring-side subsystem 150 includes, for example, at least one information transceiver interface and processing unit 154, which, for example, includes an information transceiver interface for receiving at least one signal string transmitted by the monitoring equipment 122 and sending out a response signal. The information transceiver interface and processing unit 154 can be implemented with conventional technology, for example, through the combination of servers, but is not limited to a particular method. In addition, the information transceiver interface and processing unit 154 further includes at least one signal processing unit which processes the received signal string so as to obtain at least one information content carried by the signal string, and meanwhile, processes the content to be sent into a response signal. The information content includes video/audio signals as well as signals examined by instruments, which may be, for example, physiological examination information or physical examination information.

The monitoring-side subsystem 150 further includes at least one video/audio unit 156 for receiving the video/audio content of the information content to display in the display area, for example, the accident scene displayed and the audio communication. The display area may also display the signals examined by the instruments.

The monitoring-side subsystem 150 further includes at least one video conference equipment for, for example, communicating, examining, and directing emergency processing instantly with the spot-side subsystem 120 and the first-aid-side subsystem. The director 152 or other related personnel can communicate, examine, and direct emergency processing instantly through the video conference equipment.

FIG. 3 is a diagram illustrating the implementation of a monitoring equipment 122 according to an embodiment of the present invention. Referring to FIG. 3, besides being disposed at a place to capture video of an area of fixed range, the video capturing unit 122a may also be carried by the on-site worker 134 with, for example, the audio unit 122b. As a result, the processing status can be sent back to the director 152 or the medical director of the monitoring-side subsystem 150, or any other related personnel, instantly. To allow the on-site worker 134 to have a large processing space, preferably, wireless connection is adopted for the connections between the video capturing unit 122a with the audio unit 122b and the signal processing unit 122d. However, cable connection may also be used. After the signal processing unit 122d receives the signals received from the video capturing unit 122a, the audio unit 122b, and the instrument interface unit 122c, the signals are processed and converted into transmissible signal strings which can be transmitted to the communication network through the wireless connection or cable connection as described above. In other words, the signal processing unit 122d may also include receiving and sending signals with wireless or cable connection through the communication network.

Figure 4:
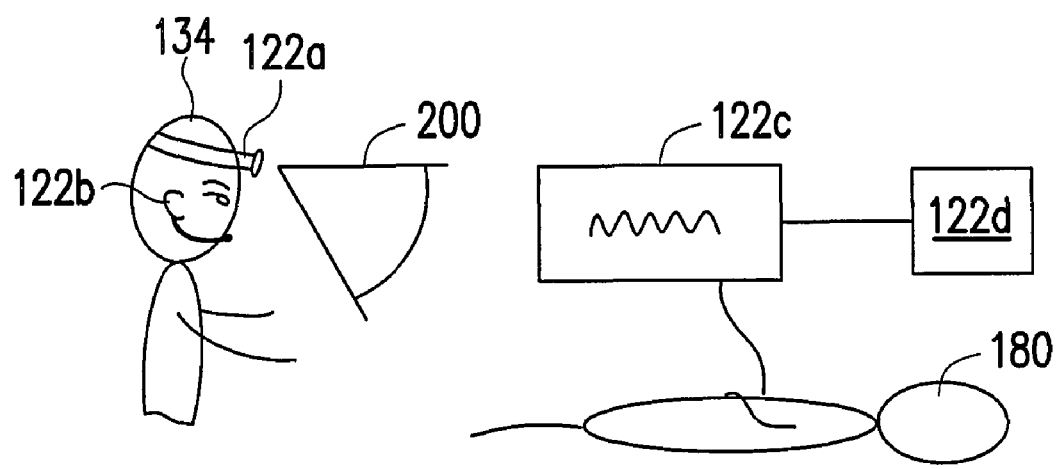
FIG. 4 is a diagram illustrating a first-aid implementation of a monitoring equipment 122 according to an embodiment of the present invention.

FIG. 4 is a diagram illustrating a first-aid implementation of a monitoring equipment 122 according to an embodiment of the present invention. Referring to FIG. 4, when the on-site worker 134 is performing clinical operation to the casualty 180, the physiological signals, such as the electrocardiogram, produced by medical instruments can be transmitted to the signal processing unit 122d by the instrument interface unit 122c. Here, the video capturing unit 122a captures the video within the capturing range 200, wherein the physiological signals, including vital-sign signals, of the casualty 180 can be captured as well as the situation thereof. Regardless of the method used, the medical director at the remote side can direct the on-site worker 134 to process appropriately through conversing over the audio unit 122b, and the medical director can see the response of the casualty after the process. For example, the process of heart electroshock requires instant instruction. The remote medical personnel can direct the on-site worker 134 to perform, for example, heart electroshock operation, through the equipment in the present invention. Conventionally, because the heart electroshock operation is highly risky, it has to be performed after transporting back to the hospital if there is no doctor on the spot, so that the best rescuing timing may be missed.

Figure 5:
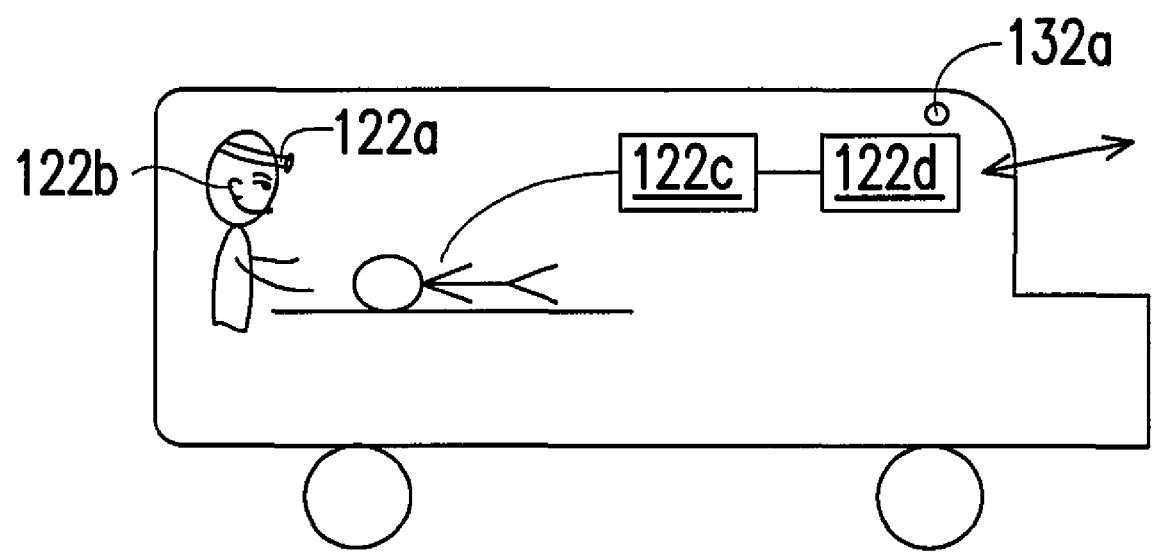
FIG. 5 is a diagram illustrating another first-aid implementation of a monitoring equipment 122 according to an embodiment of the present invention.

FIG. 5 is a diagram illustrating another first-aid implementation of a monitoring equipment 122 according to an embodiment of the present invention. Referring to FIG. 5, the monitoring equipment 122 may be, for example, disposed in an ambulance. The location of the ambulance can be provided by the GPS 132a on the ambulance. It can be understood that the communication equipment, such as the video capturing unit 122a and the audio unit 122b, can be disposed at proper place according to the actual requirement besides being worn on the head, thus, the disposition locations thereof can be arranged differently.

As to the actual possible operations, a portable physiological monitor, a network camera, a microphone, a GPS, a wireless communication network card, and a controller can be further disposed in the ambulance besides the equipment specified in the "Ambulance Equipment Standard" issued by the public health bureau.

The portable physiological monitor can be used for, for example, examining physiological parameters such as electrocardiogram, CO2, blood oxygen saturation (SpO2), non-invasive blood pressure (NIBP), heart rate, etc. Various waveforms/values on the portable physiological monitor are transmitted to the controller (or computer) through a data capturing interface.

The network camera and the microphone can transmit the video/audio information at the first-aid spot and during the procedure of transferring the casualty to the controller (or computer) through a standard interface.

The GPS receiving system can receive the positioning information of the ambulance, and the information is first transmitted to the controller (or computer) and then to the control center. Satellite navigation and dispatch of the ambulance can be performed with the positioning information along with geographic information system and electronic map.

The captured various information can be transmitted to medical institute and disaster relief unit by connecting to the Internet through a wide code-division multiple access (WCDMA) wireless network card; meanwhile, the ambulance can receive the video/audio information of remote medical direction from the hospital in-responsibility.

For example, with TCP/UDP communication protocol as the basis of information transmission, an real-time/remote/multi-point information exchange platform of two-way communication and cross-platform interaction application is developed through a message-oriented middleware (MOM) for providing one-to-one, one-to-multiple, multiple-to-one, and multiple-to-multiple instant information transmission. In this platform, various physiological parameters, videos, GPS positions or other information sent from the ambulance are considered as different subjects, and an user connected to the Internet can receive all or part of the subject information based on his/her authorization set by the administrator of the control center.

Moreover, for example, with the system described above, after the direction 152 of the monitoring-side subsystem 150 has understood the situation of the casualty and the medical facility and capability can be provided by the hospital 168, the director 152 can also instruct the ambulance to change destination hospital.

Moreover, the present invention is not limited to the application in first aid. For example, an environmental disaster with no casualty caused at a remote side, for example, hazardous gas leakage or construction damage, which requires on-site personnel to process emergently. Besides, the information about damage degree is to be measured, or even engineering trucks are to be sent. In such situations, an emergency system can be set up for instant processing according to the methods provided by the present invention. In other words, the present invention is not limited to the embodiments described above and the implementations thereof.

In overview, a movable monitoring equipment is provided by the present invention, which allows on-site personnel to receive remote directions through instant transmission of video/audio, so as to give instant processing to the situation and improve first-aid efficiency.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A remote monitoring and directing system, being set up after occurrence of an event, the system comprising:
    a spot-side subsystem, a first-aid-side subsystem and a monitoring-side subsystem, transmitting information back and forth through a network, wherein the spot-side subsystem comprises:
    at least a first video capturing unit, capturing a first video signal;
    at least a first audio unit, producing and receiving a first audio communication signal for communicating with the monitoring-side subsystem;
    at least a first instrument interface unit, transmitting at least one first instrument examination signal; and
    a first signal processing unit, coupled to the first video capturing unit, the first audio unit, and the first instrument interface unit for processing the outputs and inputs of the video first capturing unit, the first audio unit, and the first instrument interface unit respectively, outputting at least one first signal string, coupled to the monitoring-side subsystem through the network;
    wherein the first-aid-side subsystem is connected to the spot-side subsystem and the monitoring-side subsystem and controlled by the monitoring-side subsystem to cooperate with the spot-side subsystem, and the first-aid-side subsystem comprises at least one first-aid unit at a movable location, the first-aid unit is an engineering truck, or an ambulance, or a first-aid station, and the first-aid unit comprises:
    at least one second video capturing unit, capturing a second video signal;
    at least one second audio unit, producing and receiving a second audio communication signal, communicating with the monitoring-side subsystem;
    at least one second instrument interface unit, transmitting at least one second instrument examination signal; and
    a second signal processing unit, coupled to the second video capturing unit, the second audio unit, and the second instrument interface unit for processing the outputs and inputs of the second video capturing unit, the second audio unit, and the second instrument interface unit respectively, outputting at least one second signal string, coupled to the monitoring-side subsystem through the network; and
    wherein the monitoring-side subsystem, directed and controlled by at least one director, comprises:
    at least one information transceiver interface, receiving the signal string or sending a response signal;
    at least one signal processing unit, processing the signal string, obtaining at least one information content carried by the signal string; and
    at least one video/audio unit, receiving a video/audio content of the information content to display and communicate.

2. The remote monitoring and directing system as claimed in claim 1 further comprising at least one video conference equipment for at least performing real-time communication and direction operations with the spot-side subsystem and/or the first-aid-side subsystem.

3. The remote monitoring and directing system as claimed in claim 2, wherein the video conference equipment provides a medical person to instantly direct a person on the spot and/or the movable location to perform clinical operation.

4. The remote monitoring and directing system as claimed in claim 1, wherein the first-aid unit of the first-aid-side subsystem moves under direction of the monitoring-side subsystem.

5. The remote monitoring and directing system as claimed in claim 4, wherein the director at the monitoring-side subsystem can decide a hospital transfer operation of the first-aid unit according to a situation of a casualty.

6. The remote monitoring and directing system as claimed in claim 1, wherein the first-aid unit of the first-aid-side subsystem is further disposed with a positioning system to provide a location of the first-aid unit instantly.

7. The remote monitoring and directing system as claimed in claim 1, wherein the movable location of the first-aid unit and the physiological information and a video of a casualty are transmitted to a reaching destination hospital.

8. The remote monitoring and directing system as claimed in claim 1, wherein the first and second video signals captured by the first and second video capturing units comprise a spot video.

9. The remote monitoring and directing system as claimed in claim 1, wherein the first and second video signals captured by the first and second video capturing units comprise an instant video of a casualty.

10. The remote monitoring and directing system as claimed in claim 1, wherein the first and second video capturing units and the first and second audio units are movable.

11. The remote monitoring and directing system as claimed in claim 1, wherein the first and second instrument examination signals of the first and second instrument interface units comprise a physiological information, and the physiological information comprises an electrocardiogram or signals produced by medical instruments.

* * * * *